(12) United States Patent
Eck et al.

(10) Patent No.: US 6,519,133 B1
(45) Date of Patent: Feb. 11, 2003

(54) FILTER FEEDTHROUGH

(75) Inventors: Stefan Eck, Hoechstadt (DE); Boris Frauenstein, Herzogenaurach (DE); Max Schaldach, Erlangen (DE)

(73) Assignee: Biotronik Mess-und Therapiegerate GmbH & Co., Berlin (DE)

( * ) Notice: Subject to any disclaimer, the term of this patent is extended or adjusted under 35 U.S.C. 154(b) by 0 days.

(21) Appl. No.: 09/889,703

(22) PCT Filed: Nov. 20, 2000

(86) PCT No.: PCT/EP00/11518
§ 371 (c)(1),
(2), (4) Date: Oct. 19, 2001

(87) PCT Pub. No.: WO01/37929
PCT Pub. Date: May 31, 2001

(30) Foreign Application Priority Data

Nov. 20, 1999 (DE) .......................................... 199 57 189

(51) Int. Cl.⁷ ................................................. H01G 4/35
(52) U.S. Cl. .................... 361/302; 361/303; 361/301.3; 361/306.1; 361/306.2; 333/182; 333/183
(58) Field of Search ................................ 361/302, 303, 361/306.1, 309, 306.2, 307, 320, 321.6, 321.5, 301.3, 305; 333/183, 182

(56) References Cited

U.S. PATENT DOCUMENTS

| | | | |
|---|---|---|---|
| 4,152,540 A | | 5/1979 | Duncan |
| 4,853,824 A | * | 8/1989 | Tsuzurahara |
| 5,333,095 A | | 7/1994 | Stevenson |
| 5,650,759 A | * | 7/1997 | Hittman et al. |
| 5,750,926 A | * | 5/1998 | Schulman et al. |
| 5,825,608 A | * | 10/1998 | Duva et al. |
| 5,870,272 A | | 2/1999 | Seifried |
| 5,896,267 A | * | 4/1999 | Hittman et al. |
| 6,275,369 B1 | * | 8/2001 | Stevenson et al. |
| 6,424,234 B1 | * | 7/2002 | Stevenson |

FOREIGN PATENT DOCUMENTS

| | | |
|---|---|---|
| DE | 897 727 | 3/1953 |
| DE | 1 948 358 | 7/1964 |
| DE | 38 09 009 A1 | 9/1989 |
| DE | 198 19 797 A1 | 12/1998 |
| EP | 0 331 959 A2 | 9/1989 |
| EP | 0 776 016 A2 | 5/1997 |
| EP | 0 916 364 A2 | 5/1999 |
| WO | WO97/41923 A1 | 11/1997 |

* cited by examiner

Primary Examiner—Chaun N. Nguyen
Assistant Examiner—Nguyen Ha
(74) Attorney, Agent, or Firm—Stephen L. Grant; Hahn Loeser + Parks, LLP

(57) ABSTRACT

This invention relates to a unipolar or multipolar electrical filter feedthrough device (1) to be introduced into an aperture of housing (26) of an implantable electronic therapeutic device with a feedthrough body (2) to be inserted in the aperture and comprising a fixing means (3) to connect with the housing wall, and with filter means (7) designed as capacitors, that are, on one side, connected—in an electrically conductive manner—with one of the electrical pins (8) that are mutually electrically separated, and, on the other side, with the housing of the therapeutic device carrying a reference potential. Filter means (7) are arranged outside the feedthrough body (2) and are connected with this body in such a manner that they basically stick out into the inside (4) of housing (26) in a freely suspended manner.

17 Claims, 4 Drawing Sheets

FILTER FEEDTHROUGH

This invention relates to a unipolar or multipolar electrical filter feedthrough device for an implantable electronic therapeutic device, e.g., a pacemaker. The filter feedthrough is designed to be introduced into an aperture of a housing of the therapeutic device, and comprises contact elements electrically separated from each other, a fixing means for harnessing the filter body around one wall of the housing as well as filter means that are, on one side, connected—in an electrically conductive manner—with one of the contact elements, and, on the other side, with the housing having a reference potential. The filter elements usually comprise capacitive elements. The contact elements are usually designed in the form of rod-shaped pins.

BACKGROUND OF THE ART

U.S. Pat. No. 4,152,540 describes a filter design for use with an electronic pacemaker, where a filter capacitor is introduced in a borehole in the insulation ceramic material.

Furthermore, European Patent publication EP 0 776 016 A2 reveals a filter design with a ceramic filter arrangement with capacities for implantable defibrillators and pacemakers. The filter arrangement is designed as a system of layers and is integrated in the particular device.

Another version known from the U.S. Pat. No. 5,650,016 and designed for use with implantable medical therapeutic devices comprises a filter constructed as a chip capacitor or an LC module and its integration with the device occurs through encapsulation.

However, the known electrical design versions have the disadvantage that the capacitive filter means as well as the contact areas between the electrical pins and the reference potential are made impermeable by a glass-seal. This results—especially taking into account the preassembly of the filter means—in a substantial costs of manufacturing such a design version and of the introduction of the feedthrough device into the housing of the therapeutic device to be implanted, and its subsequent check for vacuum-tightness.

In addition, it is highly disadvantageous that the filter means are firmly connected with the feedthrough device and, therefore, exposed to a high thermal load when the feedthrough device is being welded into the aperture of the housing of the electronic therapeutic device. This requires a very firm mechanic binding of the filter means with the feedthrough device and, on the other hand, it often leads to an irreversible change in the electrical parameters of the filter means, which affects—mostly in an unanticipated manner—the operation of the therapeutic device to be implanted.

Based on the shortcomings of prior art, the task of this invention is, therefore, to describe a unipolar or multipolar design of the aforementioned feedthrough device that can be manufactured in an especially cost-effective manner, and can be installed—with a relatively low thermal load of the filter means—in such a manner that a change of the electrical properties of the filter means during the assembly is excluded to a large degree.

This task is resolved by a filter design mentioned at the beginning, where the filter means are arranged outside the feedthrough device and connected with it in such a manner that, in installed condition, they basically stick out into the housing in a freely suspended manner.

SUMMARY OF THE INVENTION

The invention comprises the technical knowledge that the manufacture, assembly and vacuum leakage test of a unipolar or multipolar electrical feedthrough device with filter means after its installation in the housing of an implantable electronic therapeutic device can achieve special advantages if the feedthrough device and the electrical filter means are spatially arranged in a special manner, where a contact between the filter means and the housing wall is ensured and, at the same time, the basically non-vacuum-tight design of the used filter means need not be taken into account. This results in the advantage that the actual tightly closed element, i.e., the insulation ceramic material and its connections with the flange and the pins, can be tested for leakage tightness independently from the filter means.

According to this invention, the unipolar or multipolar electrical feedthrough device to be installed in an aperture in the housing of an implantable electronic therapeutic device comprises preferably flange-shaped fixing means that can be introduced in such an aperture and that are designed to connect the feedthrough device with the housing, and, furthermore, filter means designed as a capacitor, which are connected—in an electrically conductive manner—on the one hand, with electrical pins of the feedthrough device arranged in a from each other electrically separated manner, and, on the other hand, with the housing of the electronic therapeutic device having a reference potential, while the filter means themselves are arranged outside the feedthrough device. The filter means are connected with the feedthrough device in such a manner that they basically stick out into the housing in a freely suspended manner.

This results in a substantial advantage in that no requirements as for vacuum-tightness need to be made in relation to the filter means. Only the area of the housing, where the feedthrough device is introduced into the wall of the housing, and the feedthrough body itself must be designed in a vacuum-tight manner so that, after the therapeutic device has been implanted, no bodily fluid can enter the inside of the housing.

Another advantage is the decrease of thermal or mechanical load so that mechanical damage especially of the filter (which can not be detected or only to a limited degree) can be eliminated.

In a preferred design version according to this invention, the filter means form a filter block that is arranged on the same axis as the body of the feedthrough device. Such an arrangement results in simplification during the preassembly of the feedthrough device according to this invention.

The fixing means, designed to connect the feedthrough device with the housing of the therapeutic device to be implanted, and located on the feedthrough body, is preferably designed as a ring-shaped flange and is equipped with a metal collar extending towards the inside of the housing. The filter block is fastened at the free end of the collar without any physical integrity with the feedthrough body. The ring-shaped flange forms a sufficient buffer during the introduction of the feedthrough device into the housing aperture to allow a vacuum-tight welded connection between the feedthrough body and the housing wall. In order to achieve a stress-free connection between the feedthrough body and the filter block, i.e., a connection that is not mechanically stressed to an impermissible degree by the warmth released during the welding process, the metal collar is designed in a flexible manner. According to a preferred design version of this invention, such flexibility is achieved in a simple manner by making the metal collar of a band of lamellar structure. The lamellas are essentially uniformly arranged at the collar so that the collar has basically the shape of a crown.

During the preassembly of the feedthrough device, the filter block designed in a cylindrical shape is introduced into the space restricted by the crown-shaped collar. The shell of the filter block is then based on the inner side of the lamellas of the collar.

The contact between the lamellas and the shell of the filter block form an electrical connection between the individual filter elements assigned to each pin of the feedthrough device and the housing (with the reference potential) of the implantable electronic therapeutic device.

The filter block consists of a number of ceramic discs arranged over each other in a stack. This stack comprises a number of discs (corresponding with the same number of electrical pins) designed as metallized substrate discs and each located between two non-metallized ceramic layers in order to form capacitive filter elements of the filter block.

In order to form an electrical connection of the filter elements with the housing wall carrying the reference potential it is sufficient that each of the ceramic discs designed as a metallized substrate be connected with only one lamellas of the crown-shaped collar.

In another variant of this invention, the multipolar electrical feedthrough device comprises four electric pins so that the filter block consists of four disks designed as coated substrate and four ceramic disks without any coating, which form—arranged in an alternating manner—the entire filter block.

An advantageous further variant of this invention comprises an additional connector pin to establish an electrical connection with the signal-generating and signal-processing unit of the electronic therapeutic device. This allows a simple connection of this unit with the reference potential.

In an advantageous design version of this invention, such a connection is designed in a band-wise manner, which results in special simplification of the preassembly of the signal-generating and signal processing unit.

Other advantageous design variants of this invention are characterized in sub-claims, and are described in detail in the following text by means of figures.

DETAILED DESCRIPTION OF THE INVENTION

Figure 1:
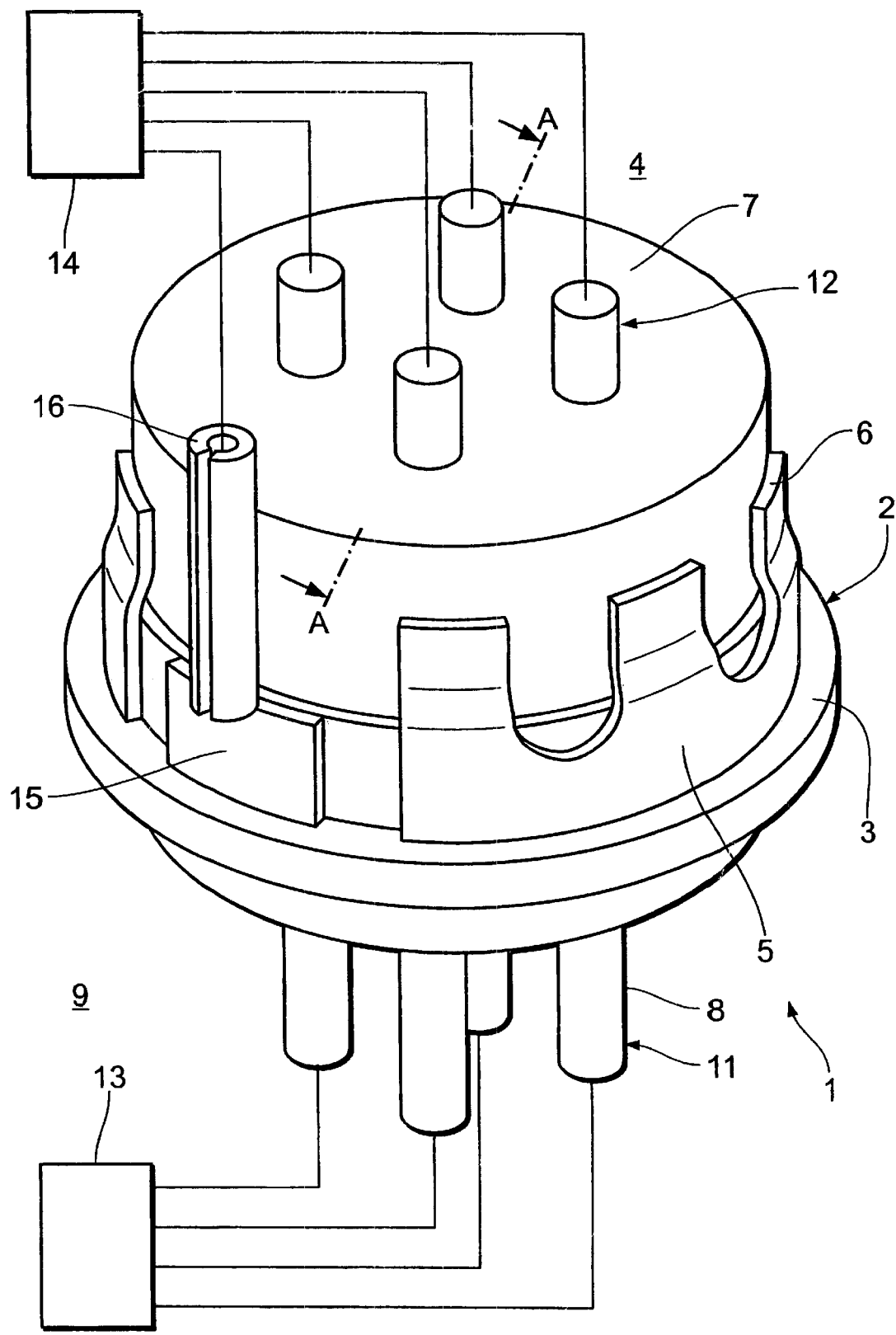
FIG. 1: A preferred design version of the invention in a perspective view.

The electrical feedthrough device 1 shown in FIG. 1 comprises an essentially cylindrical feedthrough body 2 carrying a ring-shaped flange 3. A collar 5 expanding in direction of the inner space 4 (not shown here) of a housing (cf. item 4 in FIG. 4) of an implantable therapeutic device is installed on this flange. At its free end, collar 5 ends in individual lamellas 6. Lamellas 6 are identically designed in form and size, and are uniformly distributed and arranged on the circumference of the collar. As a result, the collar has the shape of a crown, which is especially flexible in the area of its lamellas.

The inner space of this crown is filled out by the filter block 7 consisting of several capacitive filter elements (cf. items 19 to 23 in FIG. 4), which is, on its outer side, connected—in an electrically conductive manner—with individual lamellas 6.

Figure 4:
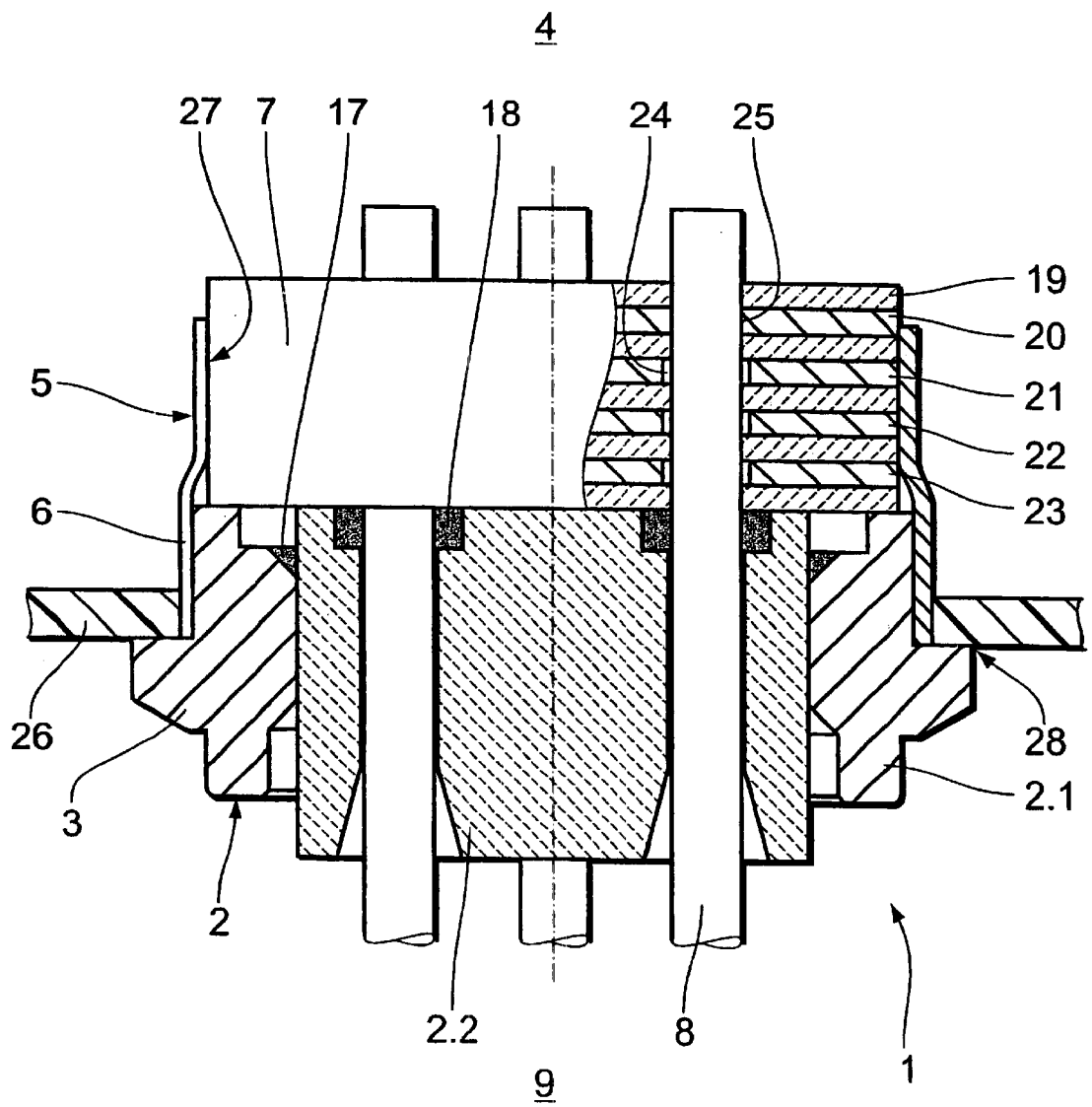
FIG. 4: Illustration of the view of a section along line A . . . A according to FIG. 1, FIG. 5: Illustration of an alternative design version as a sectional view along line A . . . A according to FIG. 1.

Pins 8, which form electric contact elements, extend from the front connection area 9 of the feedthrough device 1 to the inner space of the housing 4 and thus penetrate both the gadget body 2 and the filter block 7. FIG. 4 shows the design of the contacts of the pins inside the filter block 7 of the feedthrough device 1. Ends 11 and 12 of pins 8 are connected with a header 10 or with a signal-generating and signal-processing unit 14 of the implantable electronic therapeutic device.

A mounting plate connects an additional contact lug 16 with collar 5. The lug allows a simple connection of the signal-generating and signal-processing unit 14 with the wall of housing 26 (carrying the reference potential) of the implantable electronic therapeutic device. This arrangement simplifies the assembly of the multipolar feedthrough device.

Figure 2:
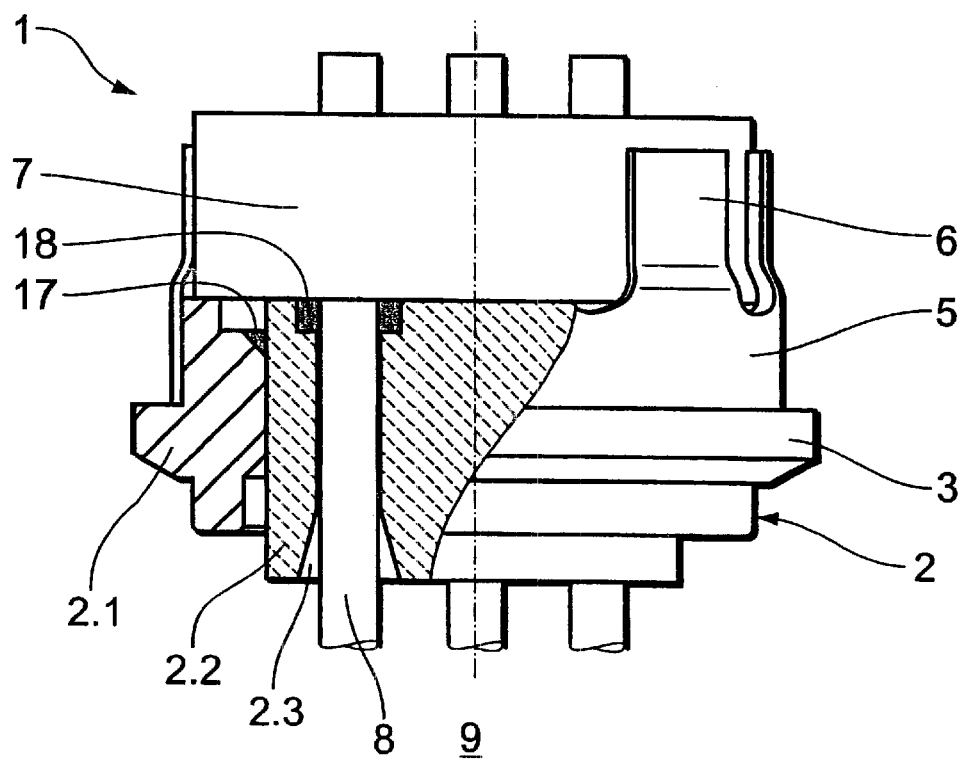
FIG. 2: The design version of this invention shown in FIG. 1 in partial sectional view from the side.
Figure 3:
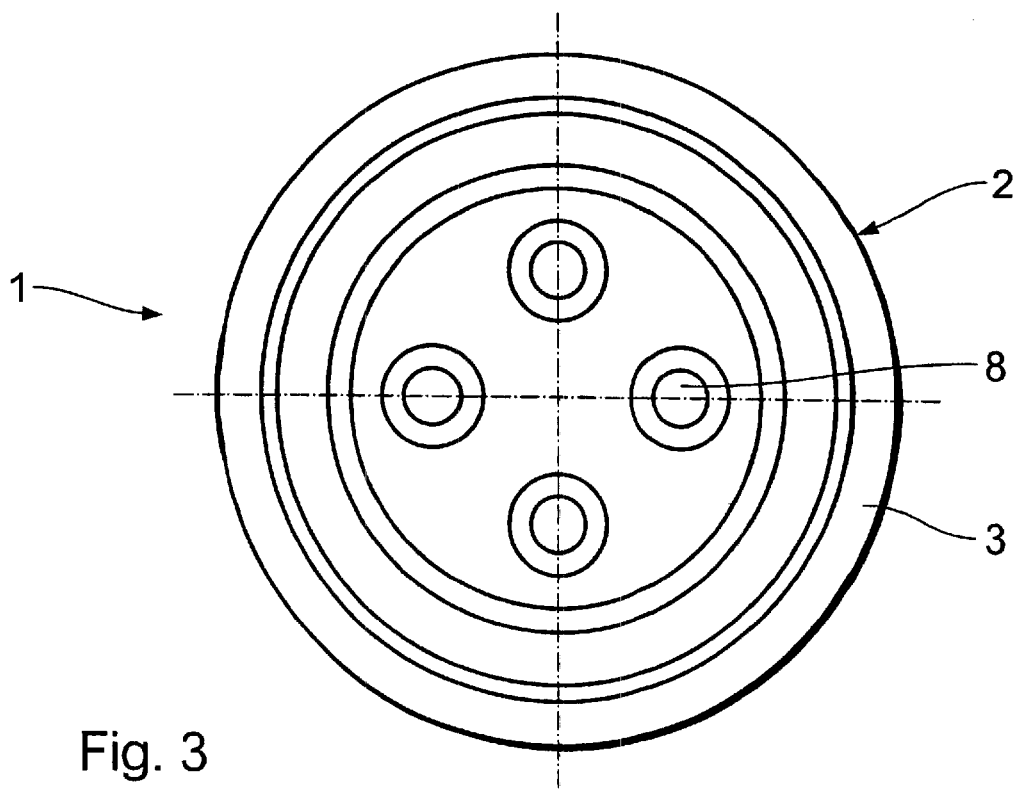
FIG. 3: The design version shown in FIG. 1 in view from below as well as [one missing line]

FIGS. 2 and 3 illustrate in detail the form of body 2 of a multipolar electrical feedthrough device 1.

Feedthrough device body 2 consists of a basically cylindrically designed shell 2.1, on which is installed a ring-shaped flange 3, and a ceramic core 2.2, which completely fills out the inner space of the shell. The mutually adjacent surface areas of shell 2.1 and ceramic core 2.2 are connected, in a vacuum-tight manner, by a sealing binding material 17 such as solder, bonding material or, as is preferred in this particular case, by gold. Pins 8 are led, in a vacuum-tight manner, in bore holes through this ceramic core. The bonding material connecting the relevant surface areas is marked with 18.

Funnel-shaped expansion 2.3 of the bore holes in ceramic core 2.2 designed for pins 8 on the header side 9 of the feedthrough device 1 allows, to a small extent, a radial mobility of the ends of the fixed pins 8 sticking out of the ceramic core which results in a simplification during the assembly of the header (cf. item 13 in FIG. 1) after feedthrough device 1 is placed in the housing of the implantable electrical therapeutic device. The main purpose of the funnel-shaped expansions also called countersinks 2.3 is the mutual electrical insulation of the pins and especially of the pin flange, since this arrangement prevents any leakage currents on the ceramic surface.

FIG. 4 shows filter block 7 of a multipolar electrical feedthrough device 1 in a schematized partial sectional view.

Filter block 7 comprises a number of ceramic disks 19, 20, 21, 22, 23 arranged above each other, of which disks 20, 21, 22, and 23 are designed as metallized substrate. Disks 19 are identically designed and arranged between two layers with metallized coating. This layer design consisting of alternating ceramic discs and metallized layers is preferably achieved with ceramic disks that are suitably metallized. Ceramic discs 19 comprise four identically wide boreholes to conduct pins 8. Discs 20, 21, 22, and 23 paired form a capacitor, where a non-metallized ceramic disc 19 placed in between them serves as a dielectric medium. Each of discs 20, 21, 23, 23, designed as metallized substrate also in identical manner, has an electric contact with just one of pins 8. For this purpose, three bore holes 24 are made in these discs, through which three pins penetrate the filter block 7, while there is a small gap between the discs and the pins. The diameter of the fourth bore hole is smaller than the diameter of bore holes 24, and essentially equals the outer diameter of pins 8. This bore hole comprises the contact spot 25 of pins 8 with the relevant metallized disc 20, 21, 22, or 23. Discs 20, 21, 22, or 23 are connected, in an electrically conductive manner, at its peripheral area, with lamellas 6 of collar 5. and thus they are in contact with wall 26 of the housing (carrying the reference potential) of the implantable electronic therapeutic device. The relevant contact spot is marked with 27.

The arrangement of lamellas 6 at the free end of the collar causes a sufficient flexibility of the collar to absorb mechanical stress arising due to warmth development during the manufacture of the connection between housing wall 26 and shell 2.1 of the feedthrough body 2, without mechanically stressing the filter block. The relatively large distance between filter block 7 hovering above the feedthrough body 2 and the welding spot 28 causes that the development of warmth during the welding of feedthrough device 1 into housing 26 of the implantable therapeutic device does not result in such a thermal load of individual filter elements of filter block 7 as to change their electrical parameters in an irreversible way.

Figure 5:
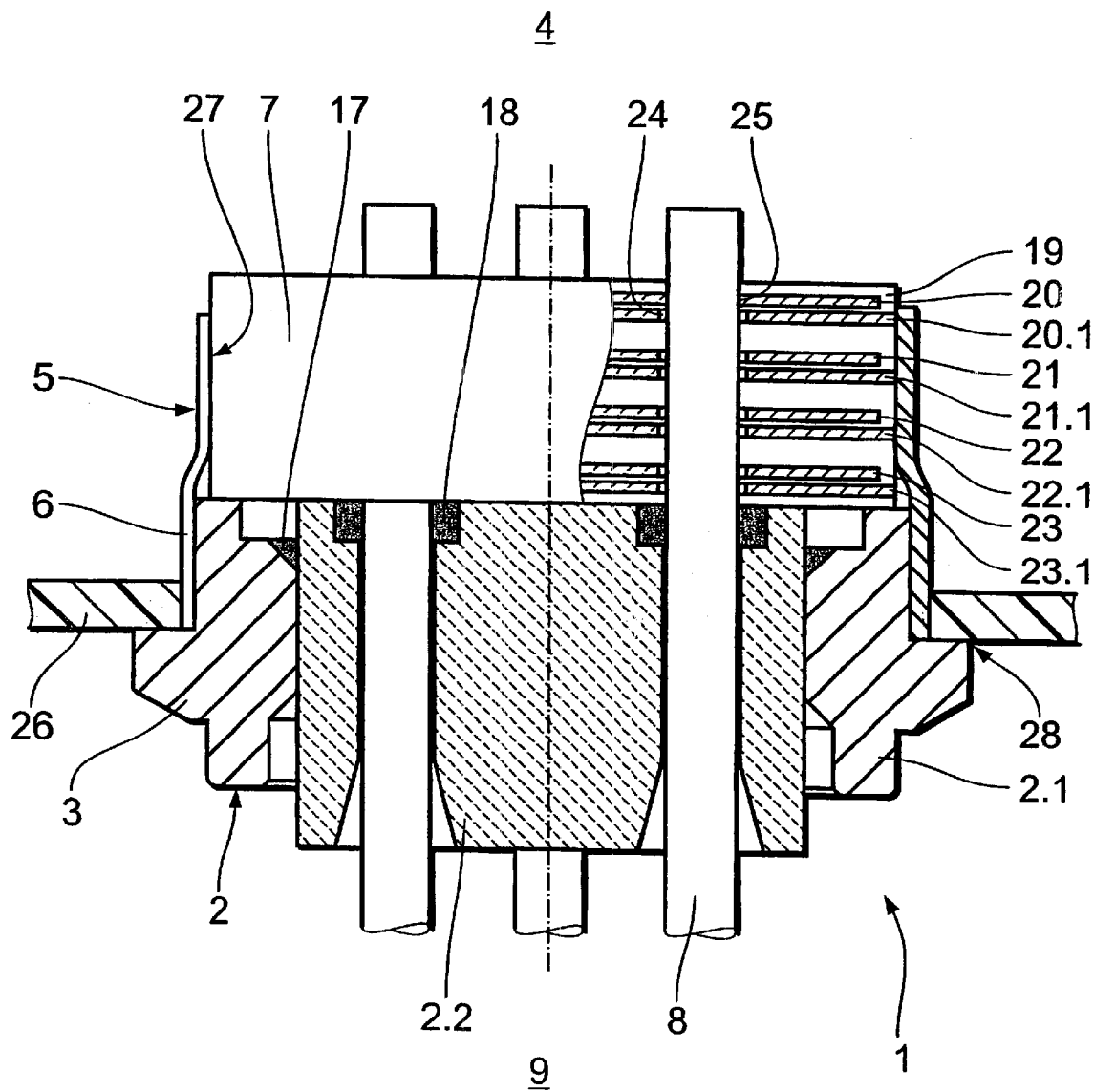

The design version of a multipolar electrical feedthrough device 1 in FIG. 5 differs from the design variant shown in FIG. 4 essentially in the structure of filter block 7.

In addition to disks 20, 21, 22, and 23, each of which is connected with one of pins 8, filter block 7 from FIG. 5 comprises four electrically conductive discs 20.1, 21.1, 22.1, and 23.1 formed by metallized substrate, that are connected, at their peripheral edge, in an electrically conductive manner, with lamellas 6 of collar 5. Unlike the variant in FIG. 4, each of discs 20, 21, 22, and 23 is connected with only one of pins 8, but not with lamellas 6 of collar 5. Discs 20, 21, 22, and 23 as well as discs 20.1, 21.1, 22.1, and 23.1 are arranged in pairs facing each other in such a manner that disc 20 faces disc 20.1, disc 21 faces disc 21.1, disc 22 faces disc 22.1, and disc 23 faces disc 23.1.

One of each disc pair is connected with one of pins 8, while the other disc is connected, in an electrically conductive manner, with collar 5. Each of disc pairs 20, 20.1, and 21, 21.1, and 22, 22.1, and 23, 23.1 forms a capacitor connected between one of pins 8 a collar 5.

The bore holes 24 in discs 20, 20.1, 21, 21.1, 22, 22.1, 23, and 23.1 are designed in such a manner that always exactly one bore hole 24 in discs 20, 21, 22, and 23 is so narrow that the relevant disc (of discs 20, 21, 22, and 23) contacts the corresponding pin 8, while all remaining bore holes, especially all bore holes 24 in discs 20.1, 21.1, 22.1, and 23.1 have a larger diameter so that these discs have a certain distance from the aforementioned pin 8 and have no electrical contact with it.

FIGS. 1 to 5 describe multipolar electrical feedthrough devices. Unipolar filter feedthrough devices can be fabricated in a similar manner as the described multipolar designs. So the unipolar design can comprise, e.g., only one pin of the type of pins 8, that is, e.g., connected with a number of electrically conductive discs such as discs 20, 21, 22, and 23, while a second type of discs such as electrically conductive discs 20.1, 21.1, 22.1, are connected, in an electrically conductive manner, with collar 5. This invention is not restricted to the preferred design examples described in previous text. There exist a number of variants that make use of the presented solution even if they contain some other substantially differing design.

What is claimed is:

1. Unipolar or multipolar electrical filter feedthrough device for insertion in an aperture in a housing of an implantable electronic therapeutic device, the feedthrough device comprising:

a feedthrough body to be installed in the aperture, with at least one mutually electrically separately arranged contact elements, and a fixing means for the connection with a wall of the housing, and filter means connected, in an electrically conductive manner, on the one hand, each with one of the said contact elements and, on the other hand, with the housing carrying a reference potential, wherein the fixing means is a flange comprising a flexible metal collar having lamellas and a free end, extending towards the inside of the housing with the filter means arranged outside the feedthrough body on the free end, and wherein the filter means are connected with the feedthrough body to stick out into the housing inside in a freely suspended manner.

2. The feedthrough device of claim 1, wherein the filter means form a filter block on the same axis with the feedthrough body.

3. The feedthrough device of claim 1, wherein the filter block is installed on the free end of the metal collar.

4. The feedthrough device of claim 1, characterized in that the lamellas are essentially uniformly distributed and arranged on the collar.

5. The feedthrough device of claim 4, characterized in that the metal collar has the shape of a crown.

6. The feedthrough device of claim 1, characterized in that the shell of filter block is based on the inner side of lamellas.

7. The feedthrough device of claim 2, wherein the filter block comprises a plurality of ceramic discs arranged in layers, where a plurality of contact elements corresponding to the relevant number of discs are designed as metallized substrate, and are each placed between two non-metallized ceramic discs.

8. The feedthrough device of claim 5, wherein some of the metallized substrate discs are connected in an electrically conductive manner with at least one lamella.

9. The feedthrough device of claim 8, wherein the feedthrough body comprises four electrical pins as contact elements.

10. The feedthrough device of claim 9, wherein one pin is always connected, in an electrically conductive manner, with just one metallized substrate disc.

11. The feedthrough device of claim 10, characterized in that the metallized substrate discs, comprise a number of borehole to conduct a corresponding number of pins.

12. The feedthrough device of claim 11, characterized in that the bore holes in the metallized substrate discs are made in such a manner that that bore hole in one of the metallized substrate discs has a smaller diameter than the remaining bore holes, which contains the one of pins that is electrically connected with the particular disc.

13. The feedthrough device of claim 1, wherein the collar comprises an additional contact lug for electrical connection of a signal-generating and signal-processing unit of the implantable electronic therapeutic device with the wall of the housing.

14. The feedthrough device of claim 13, wherein the contact lug is in a band shape.

15. An implantable electronic therapeutic device with a housing and an a signal-generating and signal-processing unit arranged in such housing characterized by a unipolar or multipolar electrical filter feedthrough device to connect the electronic signal-generating and signal-processing unit with the signal and control links required for the operation of the therapeutic device, wherein the feedthrough device comprises:

a feedthrough body to be installed in an eperture in the housing, with at least one mutually electrically separately arranged contact elements, and a fixing means for the connection with a wall of the housing, and filter means connected, in an electrically conductive manner, on the one hand, each with one of the said contact elements and, on the other hand, with the housing carrying a reference potential, wherein the fixing means is a flange comprising a flexible metal collar having lamellas and a free end, extending towards the inside of the housing with the filter means arranged outside the feedthrough body on the free end, and wherein the filter means are connected with the feedthrough body to stick out into the housing inside in a freely suspended manner.

16. The feedthrough device of claim 1, wherein the filter block is installed on the free end of the metal collar.

17. The feedthrough device of claim 1, wherein the filter means comprises at least one capacitor.

* * * * *